United States Patent [19]
Ostroff

[11] Patent Number: 5,622,940
[45] Date of Patent: Apr. 22, 1997

[54] INHIBITION OF INFECTION-STIMULATED ORAL TISSUE DESTRUCTION BY β(1,3)-GLUCAN

[75] Inventor: Gary R. Ostroff, Worcester, Mass.

[73] Assignee: Alpha-Beta Technology, Worcester, Mass.

[21] Appl. No.: 274,955

[22] Filed: Jul. 14, 1994

[51] Int. Cl.$^6$ ............................ A61K 31/715; C07H 1/00
[52] U.S. Cl. ............................ 514/54; 514/835; 514/885; 514/900; 514/901; 514/902; 536/123.1; 536/123.12
[58] Field of Search ............................ 514/54, 835, 885, 514/900, 901, 902; 536/123.1, 123.12

[56] References Cited

U.S. PATENT DOCUMENTS

| | | | |
|---|---|---|---|
| 3,931,398 | 1/1976 | Gaffar et al. | 424/92 |
| 3,943,247 | 3/1976 | Komatsu et al. | 424/180 |
| 4,138,479 | 2/1979 | Truscheit et al. | 424/88 |
| 4,237,266 | 12/1980 | Sugiura et al. | 536/1 |
| 4,430,322 | 2/1984 | Stoudt et al. | 424/49 |
| 4,471,402 | 9/1984 | Williams et al. | 514/54 |
| 4,707,471 | 11/1987 | Larm et al. | 514/54 |
| 4,739,046 | 4/1988 | Di Luzio | 536/117 |
| 4,810,646 | 3/1989 | Jamas et al. | 536/123 |
| 4,833,131 | 5/1989 | Williams et al. | 514/54 |
| 4,900,722 | 2/1990 | Williams et al. | 514/54 |
| 4,973,472 | 11/1990 | Morisaki | 424/48 |
| 5,032,401 | 7/1991 | Jamas et al. | 424/426 |
| 5,328,829 | 7/1994 | Stashenko | 435/7.9 |

FOREIGN PATENT DOCUMENTS

| | | |
|---|---|---|
| 55-071701 | 8/1980 | Japan. |
| 56-076401 | 9/1981 | Japan. |
| 59-045301 | 6/1984 | Japan. |
| 59-210901 | 4/1985 | Japan. |
| 2076418 | 12/1981 | United Kingdom. |
| 91/03495 | 3/1991 | WIPO. |
| 91/03248 | 3/1991 | WIPO. |
| 92/13896 | 8/1992 | WIPO. |
| 94/04163 | 3/1994 | WIPO. |

OTHER PUBLICATIONS

*Goodman and Gilman's The Pharmacological Basis of Therapeutics*, Ed. Gilman et al., 8th Edition, p. 1029, (1990).

Stashenko, P., et al., "Inhibition of Periapical Bone Resorption by a Biological Response Modifier", *J. Dent. Res.* 73 (IADR Abstracts) 1994; Abstract 146.

Manners, D.J., et al., "The Structure of a β-(1→3)-D-Glucan from Yeast Cell Walls," *Biochem. J.*, 135:19–30 (1973).

Onderdonk, A.B., et al., "Anti–Infective Effect of Poly–β1–6–Glucotriosyl–β1–3–Glucopyranose Glucan In Vivo," *Infec. Immun.*, 60(4):1642–1647 (1992).

Williams, D.L., et al., "Pre-clinical Safety Evaluation of Soluble Glucan," *Int. J. Immunopharmac.*, 10(4):405–414 (1988).

Janusz, M.J., et al., "Isolation of Soluble Yeast β–Glucan that Inhibit Human Monocyte Phagocytosis Mediated by β–Glucans Receptors," *J. Immunol.*, 137:3270–3276 (1986).

Miyazaki, T., et al., "Structural Examination of Antitumour, Water–Soluble Glucans from *Grifora umbellata* by Use of Four Types of Glucanese," *Carbohydrate Research*, 65:235–243 (1978).

Reiskind, J.B. and Mullins, J.T., "Molecular Architecture of the Hyphal Wall of *Achlya ambisexualis* Raper. II. Ultrastructural Analyses and a Proposed Model," *J. Microbiol.*, 27:1100–1105 (1981).

Sherwood, E.R., et al., "Soluble Glucan and Lymphokine–activated Killer (LAK) Cells in the Therapy of Experimental Hepatic Metastases," *Chemical Abstracts*, 108:179752V (1988).

Williams, D.L., et al., "Pre–clinical Safety Evaluation of Soluble Glucan," *Chemical Abstracts*, 109:66566q (1988).

Williams, D.L., et al., "Development of a Water–Soluble, Sulfated (1→3)–β–D–Glucan Biological Response Modifier Derived from *Saccharomyces cerevisiae*," *Carbohydrate Research*, 235:247–257 (1992).

Hara, C., et al., "A Branched (1→3)–β–D–Glucan From a Water Extract of *Dictyophora indusiata* FISCH," *Carb. Res.*, 145:237–246 (1986).

Fleet, G.H., et al., "Isolation and Composition of an Alkali–soluble Glucan from the Cell Walls of *Saccharomyces cerevisiae*," *Journal of General Microbiology*, 94:180–192 (1976).

Sherwood, E.R., et al., "Enhancement of Interleukin–1 and Interleukin–2 Production by Soluble Glucan," *Int. J. Immunopharmac.*, (3):261–267 (1987).

Fleet, G.H., et al., "Isolation and Composition of an Alkali–Soluble Glucan from the Cell Walls of *Saccharomyces cerevisiae*," *Chemical Abstracts*, 85:89819z (1976).

Bacon, J., et al., "The Glucan Components of the Cell Wall of Baker's Yeast (*Saccharomyces cerevisiae*) Considered in Relation to its Ultreastructure," *Biochem. J.*, 114:557–567 (1969).

Goldman, R., "Induction of a β–1, 3–D–Glucan Receptor in P388D1 Cells Treated with Retinoic Acid of 1,25–dihydroxyvitamin $D_3$," *Immunology*, 63:319–324 (1988).

Bacon, J.S.D., et al., "Glucan Components of the Cell Wall of Bakers' Yeast (*Saccharomyces cerevisiae*) Considered in Relation to its Ultrastructure," *Chemical Abstracts*, 71:109168c (1969).

Konopski, Z., et al., "Phagocytosis of β–1,3–D–Glucan–Derivatized Microbeads by Mouse Peritoneal Macrophages Involves Three Different Receptors," *Scand. J. Immunol.*, 33:297–306 (1991).

(List continued on next page.)

Primary Examiner—John Kight
Assistant Examiner—Howard C. Lee
Attorney, Agent, or Firm—Hamilton, Brook, Smith and Reynolds, P.C.

[57] ABSTRACT

Methods of treating or preventing infection-induced oral tissue destruction or gingivitis in a mammal, comprising administering a therapeutically effective amount of a β(1,3)-glucan, such as poly-β(1-6)-glucotriosyl-β(1-3)-glucopyranose glucan (PGG-glucan), are disclosed.

30 Claims, 2 Drawing Sheets

OTHER PUBLICATIONS

Pretus, H.A., et al., "Isolation, Physicochemical Characterization and Preclinical Efficacy Evaluation of Soluble Scleroglucan," *The Journal of Pharmacology and Experimental Therapeutics*, 500–510 (1991).

Williams, D.L., et al., "Development, Physicochemical Characterization and Preclinical Efficacy Evaluation of Water Soluble Glucan Sulfate Derived from *Saccharomyces cerrevisiae*," *Immunopharmacology*, 22:139–156 (1991).

Williams, D.L., et al., "A Sequential Multi–Assay Protocol for the Preclinical Assessment of Natural Product Complex Carbohydrate Immunomodulators," *Develop. Biol. Standards.*, 77:129–136 (1992).

Browder, W., et al., "Beneficial Effect of Enhanced Macrophage Function in the Trauma Patient," *Ann. Surg.*, 605–613 (1990).

Chihara, G., et al., "Lentinan as a Host Defense Potentiator (HPD)," *Int. J. Immunotherapy*, V(4):145–154 (1989).

Stashenko, P., et al., "Inhibition of Periapical Bone Resorption by a Biological Response Modifier PGG Glucan", *J. Dent. Res.* 74(1):323–330 (1995).

INHIBITION OF INFECTION-STIMULATED ORAL TISSUE DESTRUCTION BY β(1,3)-GLUCAN

BACKGROUND OF THE INVENTION

Pulpal and periodontal diseases are bacterial infections which result in local connective tissue and bone destruction. The microorganisms which have been implicated as pathogens in these diseases are primarily gram negative anaerobes, which include *Actinobacillus actinomycetemcomitans, Porphyromonas gingivalis, Prevotella intermedia,* and *Campylobacter recta* (Dzink, J. L., et al., *J. Clin. Periodontol.* 15:316–323 (1988)). Although these infections stimulate both specific T and B cell-mediated (Ebersole, J. L., et al., *J. Periodont. Res.* 22:184–186 (1987); Stashenko, P., et al., *J. Periodont. Res.* 18:587–600 (1983)) and non-specific (neutrophils, monocytes and cytokines) host responses, most data support a key role for the non-specific arm, in particular neutrophils and other phagocytic cells, in host defense against these microorganisms (Genco, R. J., *J. Periodontol.* 63:338–355 (1992); Van Dyke, T. E., and G. A. Hoop, *Crit. Rev. Oral Biol. Med.* 1:117–133 (1990)). This is illustrated by findings that individuals with neutrophil defects, including chronic granulomatous disease, cyclic neutropenia, Papillon-Lefevre syndrome, leukocyte adhesion deficiencies, and Chediak-Higashi syndrome exhibit dramatically increased incidence and severity of periodontal destruction (Barrett, A. P., et al., *Oral Surg. Oral Med. Oral Path.* 69:174–176 (1990); Bauer, W. H., *J. Dent. Res.* 25:501–508 (1946); Cohen, M. B., et al., *J. Periodontol.* 56:611–617 (1985); Cohen, D. W., and A. L. Morris, *J. Periodontol.* 32:159–168 (1961); Tempel, T. T., et al., *J. Periodont. Res.* 7 *(Suppl* 10):26–27 (1972); Van Dyke, T. E., et al., *Clin. Immunol. Immunopathol.* 31P:419–429 (1984)).

Current treatments for human periodontal disease focus on debridement and surgery to reduce the microbial load and enhance the ability of the patient to maintain infected sites. Because periodontal disease is now recognized as an infection by a limited spectrum of pathogens, adjunctive antimicrobials are also coming into wider usage (Slots, J., and T. E. Rams, *J. Clin. Periodontol.* 17:479–493 (1990)). A great need remains for safe and effective treatments for periodontal disease.

SUMMARY OF THE INVENTION

This invention pertains to methods of treating or preventing in a mammal infection-stimulated oral tissue destruction, including bone destruction, resorption, or loss, as well as soft tissue necrosis, destruction, or loss, as well as treating or preventing gingivitis, by administering a therapeutically effective amount of a β(1,3)-glucan, such as poly-β(1-6)-glucotriosyl-β(1-3)-glucopyranose glucan (PGG-glucan). β(1,3)-glucans are biological response modifiers which upregulate the phagocytic and bactericidal activity of neutrophils and monocytes. A therapeutically effective amount of β(1,3)-glucan is administered to the mammal in a single dose or a series of doses separated by intervals of days or weeks, such that oral tissue destruction is treated, minimized, inhibited or prevented. The β(1,3)-glucan can additionally be administered in a pharmaceutically acceptable vehicle.

Biological response modifiers such as β(1,3)-glucans provide a new therapeutic approach to preventing and treating oral bacterial infections by upregulating host antibacterial defense mechanisms. This host-oriented approach may be especially timely, given the increasing concern of bacterial antibiotic resistance which has arisen concomitant with widespread antibiotic usage. Furthermore, specific β(1,3)-glucans, such as PGG-glucan, which selectively stimulate neutrophil and monocyte anti-infective function without stimulating cytokine production, circumvent the induction of inflammatory cytokine-induced bone resorption and may thus represent ideal agents for the treatment of oral infections including periodontal disease.

DETAILED DESCRIPTION OF THE INVENTION

Figure 1:
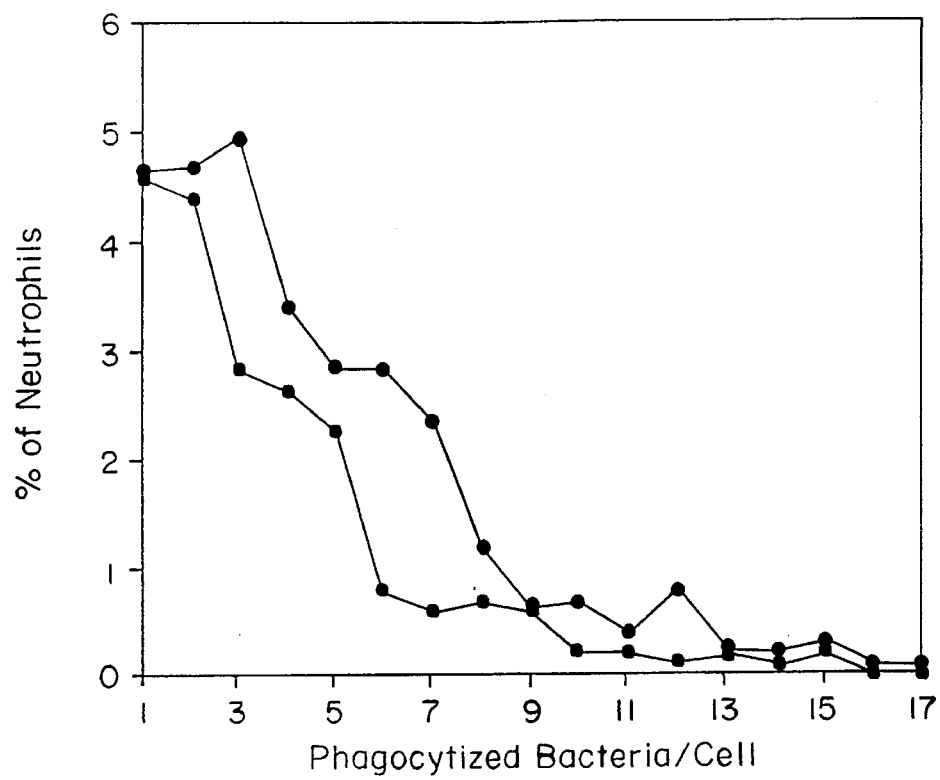
FIG. 1 demonstrates the effect of PGG-glucan on phagocytic activity of rat neutrophils. Neutrophils were obtained from the peripheral blood of rats treated with PGG-glucan (.) or saline as a control ('). Their ability to phagocytize opsonized Texas Red-labelled *Escherichia coli* was quantified by fluorescence microscopy. X-axis: number of ingested *E. coli*/cell; y-axis: proportion of cells containing ingested bacteria.

The current invention pertains to the use of a biological response modifier as a prophylactic or as a treatment for infection-stimulated oral tissue loss. It has been discovered that poly-β(1-6)-glucotriosyl-β(1-3)-glucopyranose glucan (PGG-glucan), a biological response modifier which upregulates the phagocytic and bactericidal activity of neutrophils and monocytes, limits or prevents infection-stimulated alveolar bone resorption in an in vivo model. The basic structure of PGG-glucan is a β-D-(1-3)-linked glucopyranosyl backbone with β-D-(1-6)-linked side chains, of approximately 100 kD molecular weight (Jamas, S., et al., *Abstr. Int. Congr. Infect. Dis.* 698:143 (1990)). For further description of PGG-glucan, see U.S. patent application Ser. No. 07/934,015, filed Aug. 21, 1992, the entire teachings of which are incorporated herein by reference. PGG-glucan increases neutrophil production and primes phagocytic and bactericidal activity in vivo (Shah, P. M., et al., *Abstr. Int. Cong. Infect. Dis.* (1990); Mackin, W. et al., *FASEB J.* 8:A488 (1994)). Importantly, PGG-glucan does not induce proinflammatory cytokines such as interleukin-1 (IL-1) and tumor necrosis factor (TNF), thereby minimizing potentially injurious inflammatory side effects (Dinarello, C. A. *Abstr. Int. Cong. Infect. Dis.* (1990)). To date, negligible toxicity has been associated with the use of this material in either animals or humans.

As described below, periapical bone resorption was induced in Sprague-Dawley rats by surgical pulp exposure and subsequent infection from the oral environment. Animals were administered PGG-glucan (0.5 mg/kg) or saline (control) subcutaneously on Days −1, 2, 4, 6, 9, 11, 13, 16 and 18 following the pulp exposure procedure (Day 0). PGG-glucan enhanced the number of circulating neutrophils and monocytes, and increased their phagocytic activity approximately two-fold. PGG-glucan-treated animals had significantly less infection-stimulated periapical bone resorption than control animals (−40.8% and −42.4% for first and second molars respectively; $p<0.01$). PGG-glucan-treated animals also had less soft tissue destruction, as indicated by decreased extent of pulpal necrosis. Only 3.3% of first molar pulps from PGG-glucan-treated animals exhibited complete necrosis, as compared to 40.6% of pulps from controls. These findings indicate that a biological response modifier which enhances endogenous antibacterial mechanisms in neutrophils can decrease infection-stimulated alveolar bone and soft tissue destruction, in vivo.

As a result of these findings, methods have been developed to treat or prevent infection-stimulated oral tissue destruction in mammals, including humans. "Oral tissue," as used herein, comprises bone and soft tissue, such as gingival tissue. "Tissue destruction", as used herein, comprises bone destruction, resorption or loss, as well as soft tissue necrosis, destruction or loss. Methods have also been developed to treat or prevent gingivitis. The terms, "treating" and "treatment", as used herein, include minimizing the development of bone resorption, bone destruction or loss, soft tissue necrosis, destruction or loss, or gingival inflammation, as well as treating existing bone resorption, bone destruction or loss, soft tissue necrosis, destruction or loss, or gingival inflammation. The terms, "preventing" and "prevention" include inhibiting and/or preventing the resorption or destruction of bone or soft tissue, or the inflammation of the gingiva. To treat or prevent oral tissue destruction or gingivitis, a therapeutically effective amount of a $\beta(1,3)$-glucan, such as PGG-glucan, is administered to the mammal. The $\beta(1,3)$-glucan can be aqueous soluble, aqueous insoluble, and/or chemically modified. A therapeutically effective amount of a $\beta(1,3)$-glucan is the amount of the $\beta(1,3)$-glucan that is necessary to significantly prevent, reduce or eliminate oral tissue destruction or gingivitis. Administration of the $\beta(1,3)$-glucan can be in the form of a single dose, or a series of doses separated by intervals of days or weeks. The term "single dose," as used herein, includes a solitary dose as well as a sustained release dose. The $\beta(1,3)$-glucan can be administered subcutaneously, intravenously, intramuscularly, orally, by spray, via localized injection (i.e., injection into the gum), topically, by oral rinse, via a slow-release compound, or via a reservoir in dosage formulations containing conventional physiologically-acceptable carriers and vehicles. The formulation in which the PGG-glucan is administered will depend at least in part on the route by which it is administered.

The preferred therapeutically effective amount is approximately 0.02–200 mg/kg/dose of $\beta(1,3)$-glucan for those embodiments for which a mg/kg dosage can be determined. For other embodiments, such as administration by oral rinse, the therapeutically effective amount is an appropriate concentration of the $\beta(1,3)$-glucan. The therapeutically effective amount will be determined on an individual basis and will be based, at least in part, on consideration of the individual's size, as well as the severity of tissue destruction or gingivitis to be treated or prevented, the method of administration, and the $\beta(1,3)$-glucan that is used. Suitable therapeutically effective amounts of PGG-glucan for humans have been established in clinical trials as described in U.S. patent application Ser. No. 07/934,015, filed Aug. 21, 1992, the entire teachings of which are incorporated herein by reference.

The $\beta(1,3)$-glucan can be administered alone, or in conjunction with another drug, such as an antibiotic. Appropriate antibiotics include anti-infective agents such as bactericidal or bacteriostatic drugs.

The invention is further illustrated by the following Exemplification.

EXEMPLIFICATION

Inhibition of Infection-Stimulated Alveolar Bone Loss in vivo

To test the potential applicability of PGG-glucan for oral infections, a rat model of induced alveolar bone loss was employed (Yu, S. M., and P. Stashenko, *J. Endondon.* 13:535–540 (1987)). In this model, periapical bone resorption is induced by surgical pulp exposure and infection from the oral environment. Periapical resorption is rapid between Days 7 and 20 after exposure (active phase), with slowed resorption thereafter (chronic phase). A mixed inflammatory cell infiltrate, dominated by neutrophils and T lymphocytes, is present. Active phase periapical tissues contain elevated levels of bone resorbing activity (Wang, C. -Y., and P. Stashenko, *J. Dent. Res.* 70:1362–1366 (1991)), which is mediated mainly by interleukin-1α (Wang, C. -Y., and P. Stashenko, *Oral Microbiol. Immunol.* 8:50–56 (1993)). This model closely resembles the microbiology, immunology, and pathogenesis of periodontitis (Tani-Ishii, N., et al., *Oral Microbiol. Immunol.*, in press (1994); Yu, S. M., and P. Stashenko, *J. Endondon.* 13:535–540 (1987)). However, given the aggressive nature of periapical destruction, it provides a more stringent test of the efficacy of a neutrophil biological response modifier in combating oral infections leading to periodontal disease.

A. Induction of Periapical Lesions

A total of 32 male Sprague-Dawley CD rats weighing 300–325 g were used. For periapical lesion induction (Yu, S. M., and P. Stashenko, *J. Endondon.* 13:535–540 (1987)), on Day 0, animals were anesthetized by the intraperitoneal injection of ketamine (80 mg/kg) and xylazine (10 mg/kg) in sterile phosphate-buffered saline (PBS), and were mounted on a jaw retraction board. Pulpal exposures were performed using a portable variable speed electric handpiece (Okada Electric Co., Los Angeles, Calif.). Exposures were made with a size ¼ round bur to the depth of the diameter of the bur, avoiding furcal perforation. Exposed teeth were left open to the oral environment. The operative procedure was carried out on the first and second mandibular molars in all animals (4 teeth/animal).

B. Glucan Treatment

Animals were randomly divided into groups of N=16, and were treated with 0.5 mg/kg of the neutrophil biological response modifier, PGG-glucan (BETAFECTIN®, Alpha-Beta Technology, Inc., Worcester, Mass.) or with sterile saline as a control. Animals were pretreated with PGG-glucan or saline the day before pulp exposures were made in mandibular first and second molars. Pulp exposures were made on Day 0. Animals subsequently received either PGG-glucan or saline on Days 2, 4, 6, 9, 11, 13, 16 and 18. Treatments were delivered by subcutaneous injection in a total volume of 0.5 ml.

C. Leukocyte Count

The efficacy of PGG-glucan treatment was monitored by changes in leukocyte counts from baseline, as previously reported (Onderdonk, A. B., et al., *Infect. Immun.* 60:1642–1647 (1992)). Heparinized blood samples were obtained from the retroorbital sinus on Days −1 and 10 to determine the effect of PGG-glucan on peripheral leukocyte counts. Samples were diluted in 2% acetic acid and total leukocyte counts were made using a hemocytometer. Blood smears were stained with Wright/Giemsa and differential counts were determined under light microscopy (×400). Differences in peripheral leukocyte counts between treatment and control groups were analyzed for statistical significance by Student's t-test. Results are shown in Table 1.

*Escherichia coli* ($2 \times 10^7$/ml; Molecular Probes, Eugene, Oreg.) were incubated with neutrophils at 37° C. for 30 minutes with constant agitation. Neutrophil-bacteria mixtures were fixed, mounted, and viewed using a fluorescence microscope (Nikon Diaphot). The number of neutrophils and ingested bacteria per cell were quantified. Data from a representative experiment are shown in FIG. 1.

Overall, the number of ingested bacteria per cell was increased approximately two-fold in PGG-glucan-treated animals (8.3±5.3 vs 4.5±3.5 bacteria/cell). In addition, the proportion of neutrophils which contained *E. coli* was greater when cells were isolated from PGG-glucan-treated rats (24.8%) compared to control rats (16.2%). These data demonstrate that neutrophils from PGG-glucan-treated ani-

TABLE 1

Differential and Total Leukocyte Counts in PGG-Glucan-Treated and Control Rats

| Group | Treatment | Animals | % Total Leukocytes | | | |
| --- | --- | --- | --- | --- | --- | --- |
| | | | Lymphocytes | Neutrophils | Macrophages | Total |
| Control | Pre | 16 | 89.4 ± 4.6$^a$ | 8.0 ± 3.7 | 2.5 ± 1.9 | 90.5 ± 17.1 |
| | Post | 16 | 86.8 ± 6.7 | 11.4 ± 6.1$^e$ | 2.4 ± 2.0 | 95.1 ± 23.1 |
| PGG-glucan | Pre | 16 | 89.8 ± 4.2 | 8.1 ± 3.7 | 2.1 ± 1.7 | 89.3 ± 16.1 |
| | Post | 15 | 78.0 ± 11.3$^{b,d}$ | 18.0 ± 8.1$^{b,d}$ | 4.7 ± 2.7$^{b,d}$ | 114.0 ± 32.0$^{c,d}$ |

$^a$Mean ± SD
$^b$p < 0.01 vs control
$^c$p < 0.05 vs control
$^d$p < 0.01 vs pretreatment
$^e$p < 0.05 vs pretreatment As shown in Table 1, PGG-glucan-treated animals exhibited elevations of approximately 25% in total circulating leukocytes on Day 10 after pulp exposure, compared to pretreatment levels (p<0.01). By comparison, control animals which received saline showed no significant elevation in total leukocytes, although there was a tendency for increased numbers on Day 10. This small increase was due to an elevation in neutrophils which may have been induced as a consequence of the pulpal infection.

Differential counts revealed that the increase in leukocytes in PGG-glucan-treated animals was due entirely to elevations in circulating neutrophils, compared to both control animals and pretreatment levels, the numbers of which were increased approximately two-fold (Table 1). In contrast, the absolute numbers of lymphocytes remained constant over the experimental period, although their relative proportions declined. These data demonstrate that PGG-glucan administration stimulates neutrophilia and monocytemia, consistent with previous reports on the effect of this biological response modifier, in vivo (Onderdonk, A. B., et al., *Infect. Immun.* 60:1642–1647 (1992)).

D. Phagocytosis Assay

The ability of PGG-glucan to modulate neutrophil antibacterial activity was determined. Neutrophils were obtained from control and PGG-glucan-treated animals, and were tested for their ability to phagocytize opsonized *E. coli* bacteria. Prior to sacrifice on Day 20, control or PGG-glucan-treated rats were bled via cardiac puncture into collection tubes containing EDTA. Neutrophils were separated from whole blood using a discontinuous Ficoll-Hypaque gradient. The neutrophil layer was isolated and contaminating erythrocytes were lysed by a brief (30 sec) exposure to double-distilled water. Neutrophils were washed three times in Hanks Balanced Salt Solution ($Ca^{+2}$, $Mg^{+2}$- free), and were resuspended to a final concentration of $2 \times 10^6$/ml. For phagocytosis, opsonized Texas Red-labelled mals are both increased in number and also exhibit enhanced phagocytic activity.

E. Radiography and Histomorphometry to Determine Pulpal Necrosis

In order to explore the mechanism of inhibition of bone resorption in PGG-glucan-treated animals, effects on soft tissue pulpal destruction were determined. Animals were sacrificed 20 days after the pulp exposure procedure by asphyxiation in a $CO_2$ chamber. Mandibles were dissected free of tissue, and radiographs were taken using a 'soft' X-ray device (Hewlitt-Packard FAXITRON Model 43855A) and high-speed, high-resolution holographic film (Kodak SO-253). Radiographs were developed using an A/T 2000 automatic developer, and were examined for the presence of periapical radiolucencies. For histomorphometry, mandibles were fixed, decalcified in EDTA, embedded in paraffin, and sectioned. Every tenth section was stained with hematoxylin and eosin. Sections chosen for analysis included the radicular pulp, the apical foramen, and the periapical region showing the most extensive resorption. The size of the resorbed area around tooth apices was quantified using an Optimas Bioscan system precalibrated with a millimeter standard. Results were expressed as $mm^2$ resorbed bone. The extent of pulpal necrosis was expressed as a ratio of the length of the radicular pulp which was necrotic, as determined by loss of cellular and nuclear detail histologically, divided by the distance from the cementoenamel junction to the root apex. Differences in pulpal necrosis between groups were determined by Chi-Square analysis.

Figure 2:
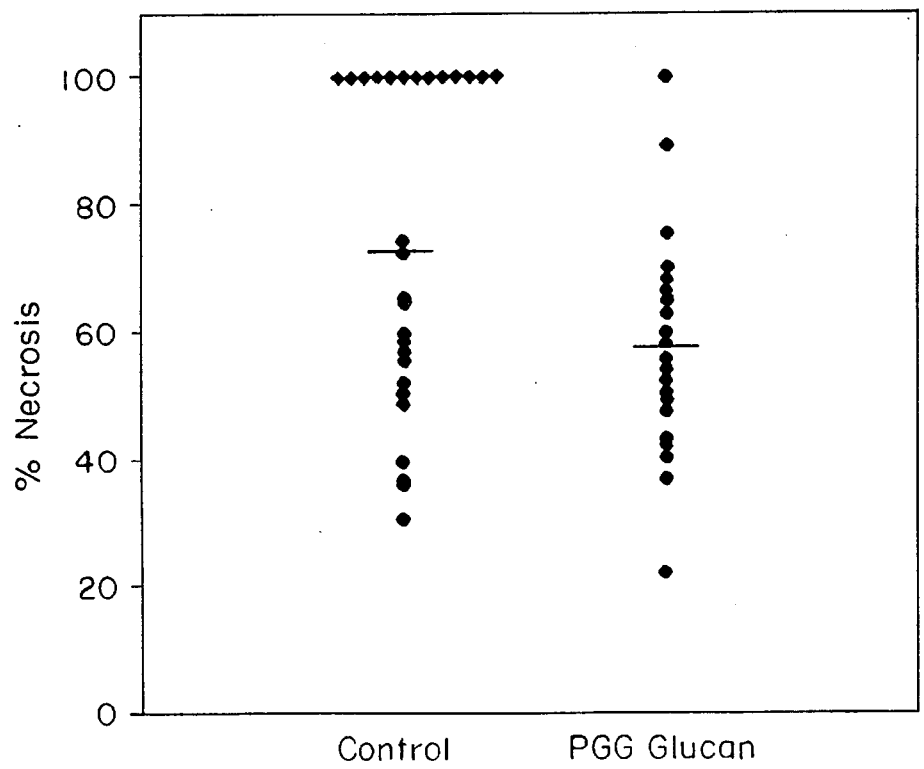
FIG. 2 demonstrates the effect of PGG-glucan on pulpal necrosis. The extent of necrosis was determined histomorphometrically on the distal root of mandibular first molars. Data represent 16 animals (2 teeth/animal) in PGG-glucan and control groups. Note the substantial number of teeth in control animals with total necrosis. Horizontal bar indicates mean.

As shown in FIG. 2, there was a significant decrease in the extent of radicular pulpal necrosis in first molars in PGG-treated animals compared to controls. Only 1 of 30 teeth (3.3%) in the PGG-glucan-treated group exhibited complete pulpal necrosis, whereas 13 of 32 teeth (40.6%) in the control group had total necrosis (p<0.001). Similar results were seen in second molars (total necrosis: 13 of 30 teeth in PGG-glucan-treated animals; 22 of 32 teeth in controls). The zone of infection and necrosis was typically limited to approximately 60% of the radicular pulp in PGG-glucan-treated animals (data not shown), with only modest periapical bone resorption. A dense inflammatory cell infiltrate was observed at the interface between necrotic and viable tissue. In contrast, control animals often had total necrosis and minimal periapical destruction (data not shown). These data suggest that the observed inhibition of bone resorption is likely to be attributable to a slowing of the rate at which the bacterial infection invades pulp tissue and progresses to the periapical region.

F. Bone Resorption Assay

Because the ultimate effect of PGG-glucan was to inhibit periapical bone destruction, it was investigated whether this agent exerts any direct modulation of osteoclastic resorption. For this purpose, the fetal rat long bone assay was utilized, which is an in vitro organ culture system which has been extensively employed to assess the bone resorptive activity of presumptive agonists. The fetal rat long bone assay was used as described, using an unpaired format (Wang, C. -Y., and P. Stashenko, *J. Dent. Res.* 22:1362–1366 (1991)). In brief, fetal bones were labeled by injecting pregnant Holzman rats with 100 µCI $^{45}$Ca (New England Nuclear, Boston, Mass.) on the 18th day of gestation. Radii and ulnae bone shafts were obtained from 19 day-old fetuses by microdissection. The bones were precultured in 0.5 ml BGJb medium for 1 day to reduce exchangeable $^{45}$Ca. Radii and ulnae were then randomized, and were cultured for 5 days in a humidified 95% air/5% $CO_2$ incubator at 37° C., with one change of medium after 2 days. Test groups consisted of 5 bones each unless otherwise noted, whereas the control group (medium only) contained 15–20 bones. The percentage of $^{45}$Ca released from each bone was determined by measuring the radioactivity in Day 0–2 medium, Day 2–5 medium, and the trichloroacetic acid-solubilized residual bone using liquid scintillation counting. For each group of bones a mean and standard deviation were computed. The significance of stimulated $^{45}$Ca release compared to control was determined using the Student's t-test. Results are shown in Table 2, below.

TABLE 2

Effect of PGG-Glucan on PTH- and IL-1-Stimulated Bone Resorption in vitro

| Stimulant | PGG-glucan (µg/ml) | | | |
|---|---|---|---|---|
| | 0 | 0.05 | 0.5 | 5 |
| Control | 19.6 ± 1.4[a] | NT[b] | 19.7 ± 0.8 | 19.7 ± 0.7 |
| PTH (4 × 10$^{-9}$M) | 65.0 ± 5.0 | 71.9 ± 12.0 | 75.7 ± 6.3 | 60.2 ± 8.5 |
| IL-1β (10 ng/ml) | 49.7 ± 16.5 | 45.3 ± 12.0 | 51.5 ± 14.5 | 43.6 ± 13.4 |

[a] % $^{45}$Ca release from prelabeled bones
[b] Not tested

As shown in Table 2, parathyroid hormone (PTH; 65±5.0%) and interleukin 1β (IL-β; 49.7±16.5%) both stimulated osteoclastic bone resorption as compared to controls (19.6±1.4%). PGG-glucan, at concentrations of 0.05–5 µg/ml, had no significant effect on basal $^{45}$Ca release, nor did it alter PTH- or IL-1-stimulated resorption. These data demonstrate that PGG-glucan does not directly modulate bone resorption in vitro, and support the interpretation that the primary effect of PGG-glucan is to enhance neutrophil function.

G. Radiographic Analysis and Histomorphometry of Bone Resorption

The effect of PGG-glucan on periapical resorption was assessed by high resolution radiography. Radiographic analysis was carried out only on the distal root of the first molar, which is most amenable to radiography due to anatomic considerations. As demonstrated in Table 3, on Day 20 after pulp exposure the area of periapical radiolucency was reduced by 48% in PGG-glucan-treated animals.

TABLE 3

Effect of PGG-Glucan on Periapical Lesion Size as Determined by Autoradiography

| PGG-Glucan-Treated (mm$^2$) | Control (mm$^2$) |
|---|---|
| 0.141 ± 0.061[a,b] | 0.271 ± 0.063 |
| N = 30 | N = 32 |

[a] Mean ± SD
[b] p < 0.01

Radiography often significantly underestimates periapical bone resorption (Bender, I. B., and S. Seltzer, *J. Am. Dent. Assoc.* 62 (Part I):153–160 (1961)). To provide a more definitive measure of periapical destruction, mandibles were processed for histomorphometry. The results are shown in Table 4 and FIG. 3.

TABLE 4

Effect of PGG-Glucan on Periapical Bone Resorption by Histomorphometry

| | N | Resorbed Area (mm$^2$) | |
|---|---|---|---|
| | | First Molar | Second Molar |
| Control | 32 | 0.316 ± 0.246[a,b] | 0.517 ± 0.390 |
| PGG-glucan | 30 | 0.187 ± 0.192[c] | 0.298 ± 0.270[c] |

Figure 3:
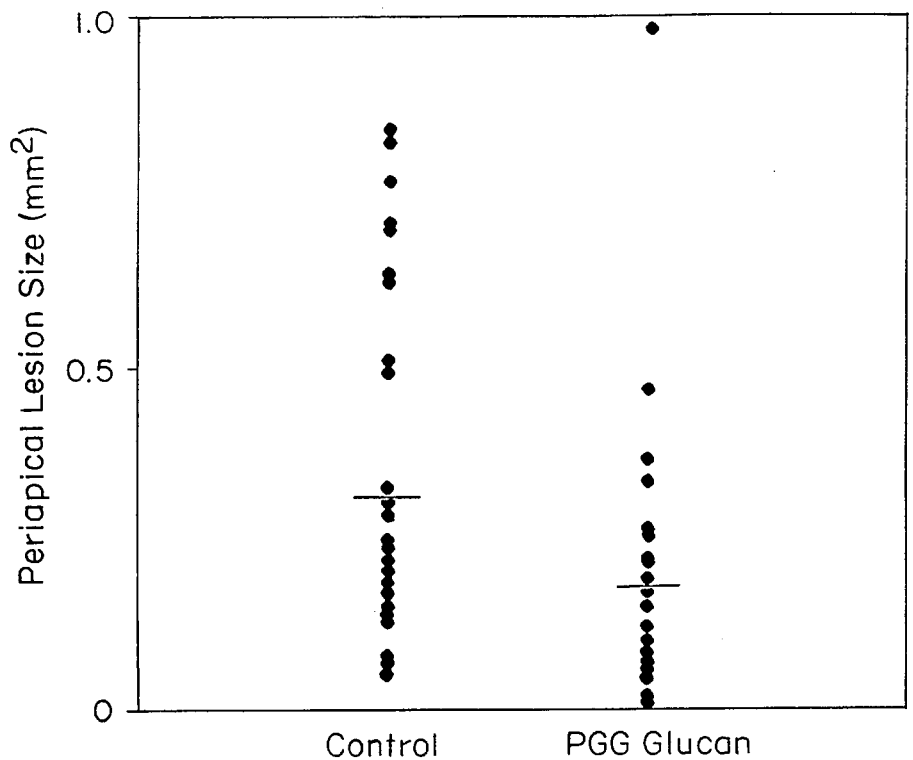
FIG. 3 demonstrates the effect of PGG-glucan on periapical bone resorption. Data shown are the area of resorption ($mm^2$) as determined histomorphometrically around the distal root of mandibular first molars. Data represent 16 animals (2 teeth/animal) in PGG-glucan and control groups. Horizontal bar indicates mean.

[a] Minus area of periodontal ligament space from unexposed teeth
[b] Mean ± SD
[c] p ≤ 0.01 vs control As shown in Table 4 and FIG. 3, direct measurement of histological sections showed that PGG-glucan-treated rats experienced significantly less periapical bone resorption around the distal roots of both the first and second mandibular molars (−40.8% and −42.4% respectively, p<0.01) than control rats. The extent of resorption associated with second molars was generally more extensive than that around first molars in both control and PGG-glucan-treated animals. This may reflect the fact that the distal root of the second molar is shorter, thus permitting more rapid progression of the infection to the periapical region.

H. Relationship between Pulpal Necrosis and Resorption

Figure 4:
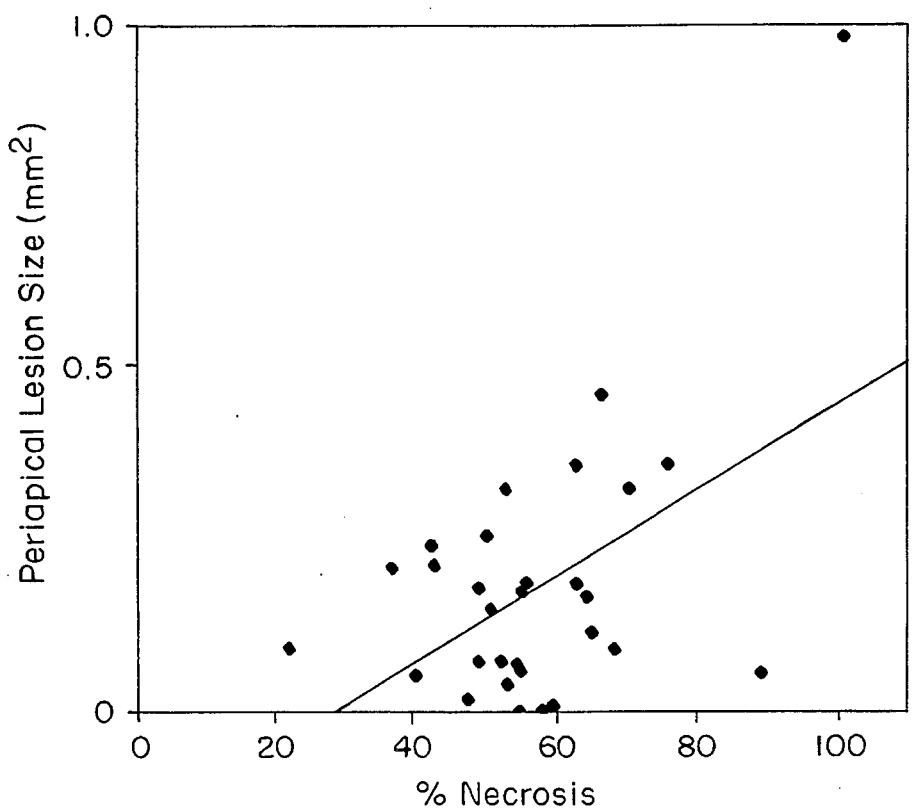
FIG. 4 demonstrates the relationship between pulpal necrosis and periapical bone resorption. X axis: proportion of necrotic pulp, distal root, first mandibular molar. Y axis: area of periapical resorption ($mm^2$). Linear regression analysis.

The relationship between pulpal necrosis and bone resorption was further explored using scatter plots and regression analysis. As shown in FIG. 4, there was a highly significant correlation between the proportion of the radicular pulp tissue which was necrotic, and the size of the resulting periapical lesion in PGG-glucan-treated animals (r=0.52, p<0.01). Both measurements were determined histomorphometrically. This relationship also held for control rats (not shown; r=0.75, p<0.001) and a similar result was obtained for second molars (not shown; p<0.001 for both control and PGG-glucan-treated groups). These findings therefore demonstrate that PGG-glucan significantly reduces the rate at which the bacterial infection invades and destroys soft tissue, and limits progression to the periapex where the infection stimulates bone resorption. The data further suggest that, in this model, periapical bone resorption correlates with the extent of pulpal necrosis.

Equivalents

Those skilled in the art will recognize, or be able to ascertain using no more than routine experimentation, many equivalents to the specific embodiments of the invention described specifically herein. Such equivalents are intended to be encompassed in the scope of the following claims:

What is claimed is:

1. A method of treating or preventing infection-stimulated oral tissue destruction in a mammal, comprising administering a therapeutically effective amount of an underivatized, aqueous soluble, β(1,3)-glucan which does not induce proinflammatory cytokines to the mammal.

2. The method of claim 1, wherein the therapeutically effective amount of β(1,3)-glucan is administered in a series of doses.

3. The method of claim 1, wherein the therapeutically effective amount of β(1,3)-glucan is administered in a single dose.

4. The method of claim 1, wherein the therapeutically effective amount of β(1,3)-glucan is 0.02–200 mg/kg per dose.

5. The method of claim 1, wherein the β(1,3)-glucan is administered in a physiologically acceptable carrier.

6. The method of claim 1, wherein the β(1,3)-glucan is administered by a route selected from the group consisting of: subcutaneously, intravenously, intramuscularly, orally, by spray, via localized injection (i.e., injection into the gum), topically, by oral rinse, via a slow-release compound, and via a reservoir.

7. The method of claim 1, wherein the mammal is human.

8. The method of claim 1, wherein the oral tissue is bone.

9. The method of claim 1, wherein the oral tissue is gingival tissue.

10. The method of claim 1, wherein the β(1,3)-glucan is administered in conjunction with an antibiotic.

11. A method of inhibiting or preventing infection-stimulated periodontal soft tissue destruction in a mammal, comprising administering a therapeutically effective amount of an underivatized, aqueous soluble, β(1,3)-glucan which does not induce proinflammatory cytokines to the mammal.

12. A method of inhibiting or preventing infection-stimulated periodontal bone destruction in a mammal, comprising administering a therapeutically effective amount of an underivatized, aqueous soluble, β(1,3)-glucan which does not induce proinflammatory cytokines to the mammal.

13. A method of inhibiting or preventing gingivitis in a mammal, comprising administering a therapeutically effective amount of an underivatized, aqueous soluble, β(1,3)-glucan which does not induce proinflammatory cytokines to the mammal.

14. A method of treating or preventing infection-stimulated oral tissue destruction in a mammal, comprising administering a therapeutically effective amount of an underivatized, aqueous soluble, β(1,3)-glucan with β(1,6) linkages which does not induce proinflammatory cytokines to the mammal.

15. The method of claim 14, wherein the therapeutically effective amount of aqueous soluble, β(1,3)-glucan with β(1,6) linkages is administered in a series of doses.

16. The method of claim 14, wherein the therapeutically effective amount of aqueous soluble, β(1,3)-glucan with β(1,6) linkages is administered in a single dose.

17. The method of claim 14, wherein the therapeutically effective amount of aqueous soluble, β(1,3)-glucan with β(1,6) linkages is 0.02–200 mg/kg per dose.

18. The method of claim 14, wherein the aqueous soluble, β(1,3)-glucan with β(1,6) linkages is administered in a physiologically acceptable carrier.

19. The method of claim 14, wherein the aqueous soluble, β(1,3)-glucan with β(1,6) linkages is administered by a route selected from the group consisting of: subcutaneously, intravenously, intramuscularly, orally, by spray, via localized injection (i.e., injection into the gum), topically, by oral rinse, via a slow-release compound, and via a reservoir.

20. The method of claim 14, wherein the mammal is human.

21. The method of claim 14, wherein the oral tissue is bone.

22. The method of claim 14, wherein the oral tissue is gingival tissue.

23. The method of claim 14, wherein the aqueous soluble, β(1,3)-glucan with β(1,6) linkages is administered in conjunction with an antibiotic.

24. A method of inhibiting or preventing infection-stimulated periodontal soft tissue destruction in a mammal, comprising administering a therapeutically effective amount of an underivatized, aqueous soluble, β(1,3)-glucan with β(1,6) linkages which does not induce proinflammatory cytokines to the mammal.

25. A method of inhibiting or preventing infection-stimulated periodontal bone destruction in a mammal, comprising administering a therapeutically effective amount of an underivatized, aqueous soluble, β(1,3)-glucan with β(1,6) linkages which does not induce proinflammatory cytokines to the mammal.

26. A method of inhibiting or preventing gingivitis in a mammal, comprising administering a therapeutically effective amount of an underivatized, aqueous soluble, β(1,3)-glucan with β(1,6) linkages which does not induce proinflammatory cytokines to the mammal.

27. The method of claim 1, wherein the underivatized, aqueous soluble, β(1,3)-glucan is derived from yeast.

28. The method of claim 11, wherein the underivatized, aqueous soluble, β(1,3)-glucan is derived from yeast.

29. The method of claim 12, wherein the underivatized, aqueous soluble, β(1,3)-glucan is derived from yeast.

30. The method of claim 13, wherein the underivatized, aqueous soluble, β(1,3)-glucan is derived from yeast.

* * * * *